United States Patent
Chin et al.

(10) Patent No.: US 10,828,332 B2
(45) Date of Patent: Nov. 10, 2020

(54) CELL-BASED COMPOSITION AND USE THEREOF FOR TREATMENT OF VERNAL KERATOCONJUNCTIVITIS

(71) Applicant: Cytopeutics Sdn. Bhd., Selangor (MY)

(72) Inventors: Bernard Sze Piaw Chin, Selangor (MY); Kong Yong Then, Selangor (MY); Soon Keng Cheong, Selangor (MY)

(73) Assignee: Cytopeutics Sdn. Bhd., Selangor (MY)

( * ) Notice: Subject to any disclaimer, the term of this patent is extended or adjusted under 35 U.S.C. 154(b) by 523 days.

(21) Appl. No.: 15/598,987

(22) Filed: May 18, 2017

(65) Prior Publication Data

US 2017/0354685 A1    Dec. 14, 2017

(30) Foreign Application Priority Data

Jun. 9, 2016  (MY) ................. 2016702124

(51) Int. Cl.
*A61K 35/28* (2015.01)
*A61K 47/02* (2006.01)
*A61K 9/00* (2006.01)
*C12N 5/073* (2010.01)

(52) U.S. Cl.
CPC ............ *A61K 35/28* (2013.01); *A61K 9/0019* (2013.01); *A61K 47/02* (2013.01); *C12N 5/0605* (2013.01)

(58) Field of Classification Search
None
See application file for complete search history.

(56) References Cited

U.S. PATENT DOCUMENTS

| | | | | |
|---|---|---|---|---|
| 6,328,960 | B1 * | 12/2001 | McIntosh | A61K 35/28 424/529 |
| 8,637,003 | B2 * | 1/2014 | Lee | A61K 35/28 424/93.7 |
| 2018/0066231 | A1 * | 3/2018 | Ikeyama et al. | C12N 5/0667 |
| 2018/0344774 | A1 * | 12/2018 | Kang | A61K 35/28 |

OTHER PUBLICATIONS

Dominici, M. L. B. K., et al. "Minimal criteria for defining multipotent mesenchymal stromal cells. The International Society for Cellular Therapy position statement." Cytotherapy 8.4 (2006): 315-317. (Year: 2006).*

McGill, James I. "A review of the use of olopatadine in allergic conjunctivitis." International ophthalmology 25.3 (2004): 171-179. (Year: 2004).*

Lu, Lu-Lu, et al. "Isolation and characterization of human umbilical cord mesenchymal stem cells with hematopoiesis-supportive function and other potentials." haematologica 91.8 (2006): 1017-1026. (Year: 2006).*

La Rosa, Mario, et al. "Allergic conjunctivitis: a comprehensive review of the literature." Italian journal of pediatrics 39.1 (2013): 18. (Year: 2013).*

Kavanagh et al "Allogeneic Mesenchymal Stem Cells Prevent Allergic Airway Inflammation by Inducing Murine Regulatory T Cells" Allergy vol. 66, pp. 523-531, 2011.

* cited by examiner

*Primary Examiner* — Robert J Yamasaki
(74) *Attorney, Agent, or Firm* — Cesari & McKenna, LLP

(57) ABSTRACT

A method for the treatment of vernal keratoconjunctivitis in a subject by administering to said subject an effective amount of a cell-based composition containing a suspension of mesenchymal stem cells in crystalloid with a cellular concentration from 0.01 million to 3.0 million cells/ml.

16 Claims, 4 Drawing Sheets

Adipogenesis

Chondrogenesis

Osteogenesis

CELL-BASED COMPOSITION AND USE THEREOF FOR TREATMENT OF VERNAL KERATOCONJUNCTIVITIS

CROSS-REFERENCE TO RELATED APPLICATIONS

The present application claims the benefit of Malaysian Application No. PI 2016702124, filed on Jun. 9, 2016, the content of which is hereby incorporated by reference in its entirety.

FIELD OF THE INVENTION

The present invention relates to a cell-based composition and use thereof for treatment of vernal keratoconjunctivitis.

BACKGROUND OF THE INVENTION

Vernal keratoconjunctivitis is an ocular surface disorder classified under the spectrum of allergic conjunctival disease. It is a chronic, usually bilateral disease mostly affecting children and adolescents. In Europe and Asia, vernal keratoconjunctivitis appears to have a prominent seasonal variation in disease expression. However, this ocular disorder seems to be less seasonal and occasionally continues until adulthood in countries of the African continent.

Patients with vernal keratoconjunctivitis are usually present with intense ocular itchiness, redness, tearing, eye discharge and photophobia. The symptoms can be extremely severe to the extent that it may profoundly affect the normal activity of a child. Many children afflicted with vernal keratoconjunctivitis are frequently absent from school due to the misinterpretation of contagious conjunctivitis by their parents or teachers. These patients commonly present with some other allergic manifestation, such as asthma, rhinitis and eczema.

Vernal keratoconjunctivitis can easily be diagnosed by clinical examination. Patients may present with palpebral, limbal or mixed manifestation. The hallmark features of palpebral vernal keratoconjunctivitis are typical giant or cobblestone papillae at the upper tarsal conjunctiva. Limbal nodules and pannus formation are among the signs of limbal vernal keratoconjunctivitis. It is often accompanied by Horner-Trantas dots that represent macro-aggregates of degenerated eosinophils and epithelial cells. Vernal keratoconjunctivitis usually run a benign course with acute exacerbations and remission. Unfortunately, the associated keratopathy can lead to sight threatening complications such as diffuse superficial punctate keratitis, shield ulcer, corneal plaque, scarring and vascularization.

At present, there is no cure for vernal allergic conjunctivitis. In efforts to treat vernal allergic conjunctivitis, management of the disease is largely aimed at controlling the disease by means of topical anti-histamine, mast cell stabiliser, steroid and ciclosporin. Most patients require long term and frequent use of topical eyedrops resulting in poor compliance. Despite these medications, the conditions in many patients may not be fully controlled. In severe cases, sub-tarsal injection of steroid, or systemic use of immunosuppressants have been prescribed in selected patients. The difficulty in compliance and proper instillation contribute to frequent exacerbations and vision-threatening complications requiring frequent hospital visits and subjecting the child to surgical procedure such as supra-tarsal corticosteroid injections. The long term use to steroid can results in glaucoma, cataract and risk of infection. In general, there is no gold standard treatment for vernal keratoconjunctivitis. An efficient new mode of therapy may control the disease with less adverse effect and suitable for paediatric age group.

In light of the above, medical experts have begun to look into other ways for treating vernal keratoconjunctivitis which is safer, non-invasive and clinically effective. Studies on mesenchymal stem cells, also known as mesenchymal stromal cells have generated a lot of interest among researchers and clinicians due to its attributes which include regenerative properties and immunomodulatory capacities. Kavanagh et al. has reported on therapy using mesenchymal stem cells and its effect in preventing allergic airway inflammation on ovalbumin (OVA) sensitized mice. It was shown that this therapy was able to reduce allergen-driven eosinophilia and suppress allergen-specific immunoglobulin E (Ig E) response. A significant reduction in levels of interleukin 4 (IL-4) and interleukin 13 (IL-13) was found but a marked increase in interleukin 10 (IL-10) inducing a regulatory T-cell population in OVA sensitized mice which were treated with mesenchymal stem cells was also observed. This illustrates that the protective effect of mesenchymal stem cells was a result of a targeted, specific immunomodulation rather than a global suppression of the immune response.

However, studies and research publications on treating vernal keratoconjunctivitis in humans using cell-based methods appears to be lacking. Accordingly, there remains a need for a novel cell-based composition which is clinically safe and therapeutically effective for treatment of vernal keratoconjunctivitis in humans.

SUMMARY OF THE INVENTION

In overcoming the above challenges resulting from conventional methods in the past, the present invention provides a cell-based preparation and its use thereof which is clinically safe and therapeutically effective for treatment of vernal keratoconjunctivitis in humans.

More particularly, the present invention relates to a cell-based composition comprising a suspension of mesenchymal stem cells in crystalloid with a cellular concentration from 0.01 million to 3.0 million cells/ml wherein the cell-based composition is used in a form of medicament for treatment of vernal keratoconjunctivitis.

Thus, one aspect of this invention is a method of treating vernal keratoconjunctivitis in a subject by administering to the subject (e.g., by intravenous infusion carried out for 0.5 to 2 hours) the cell-based composition described above and hereinafter in a therapeutically effective amount (e.g., 0.25 million to 3.0 million cells/kg body weight).

BRIEF DESCRIPTION OF DRAWINGS

The drawings constitute part of this specification and include an exemplary or preferred embodiment of the invention, which may be embodied in various forms. It should be understood, however, that the disclosed preferred embodiments are merely exemplary of the invention. Therefore the figures disclosed herein are not to be interpreted as limiting, but merely as the basis for teaching one skilled in the art of the invention.

In the appended drawings.

DETAILED DESCRIPTION OF THE INVENTION

Figure 1:
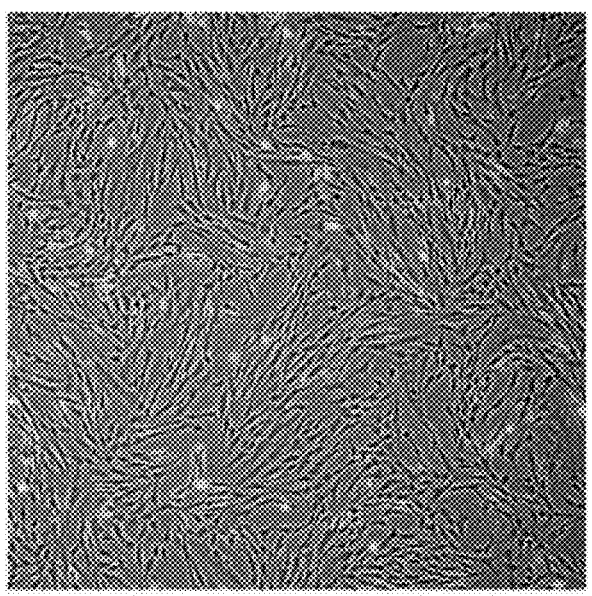
FIG. 1 illustrates morphology of human cord-derived mesenchymal stem cells.

A detailed description of the present invention is described herein. The present invention is directed to a cell-based composition and use thereof for treating vernal keratoconjunctivitis. More particularly, the present invention relates to a cell-based composition comprising a suspension of mesenchymal stem cells in crystalloid with a cellular concentration from 0.01 million to 3.0 million cells/ml wherein the cell-based composition is used in a form of medicament for treatment of vernal keratoconjunctivitis.

Accordingly, the mesenchymal stem cells used for preparation of the suspension are derived from various sources including, but not limiting to, human umbilical cord, bone marrow, fat tissue, peripheral blood or tooth pulp. Samples are either collected from mothers post-birth or from healthy donors. If required, the samples are cleaned and disinfected accordingly.

Upon collection, the samples are sent to laboratory to be processed further. The samples will be digested using a digestion enzyme, preferably, but not limiting to collagenase type II and followed by centrifugation, leaving a layer of supernatant and pellet containing mesenchymal stem cells. The mesenchymal stem cells are isolated and cultured in a specially formulated medium supplemented with a combination of various antibiotics and animal-free serum. The cultures are maintained at a temperature range from 35° C. to 40° C., preferably at 37° C. in a humidified atmosphere for 3-4 days.

As it will be apparent to a person of ordinary skill in the art, mesenchymal stem cells are adherent to plastic. Non-adherent cells are discarded and the growth medium is replaced every 3-4 days until the cells reached confluence.

Upon reaching 70%-80% confluence, the adherent mesenchymal stem cells are incubated with a dissociation enzyme, preferably, but not limiting to trypsin and re-plated at $1 \times 10^4$ cells/ml for a series of passages, preferably, but not limiting to 3-4 passages. The mesenchymal stem cells are then harvested in a culture flasks, thus expanding population of the cells.

The mesenchymal stem cells are characterized in accordance to a criteria set forth by International Society for Cellular Therapy (ISCT). Apart from adherence to plastic, established criteria defining mesenchymal stem cells include expression of antigen markers as measured by flow cytometry and tri-differentiation ability of the cells (Dominici 2006). Using flow cytometry, the mesenchymal stem cells are defined by expression of CD73, CD90, and CD105 markers whilst absence of expression for CD34, CD45, and HLA-DR markers. Meanwhile, the tri-differentiation ability of the mesenchymal stem cells is demonstrated by way of the cells differentiating into osteoblasts, adipocytes and chondroblasts.

Once the population of mesenchymal stem cells have been expanded, a disassociation enzyme, preferably, but not limiting to trypsin is added in to the flasks and incubated at a temperature range from 35° C. to 40° C., more preferably at 37° C., for a period of 1-15 minutes, more preferably for 5 minutes to detach the plastic-adherent mesenchymal stem cells, leaving the cells slightly shrunk. Next, the flasks are gently tapped to dislodge the cells and medium is further added to dilute the trypsin, forming a mesenchymal cell suspension. The cell suspension is then transferred into 50 ml centrifuge tubes and centrifuged at a speed range from 300 g to 800 g, more preferably at 500 g at a temperature range from 18° C. to 20° C. for 10 minutes forming a layer of supernatant with pellet at bottom of the tubes. The supernatant is removed, leaving the pellet of mesenchymal stem cells in the tubes.

The pellet of mesenchymal stem cells are re-suspended in a sterile cryovial of 1.8 ml in size containing cryopreservation medium comprising from 80% to 90% animal-free serum and a cryoprotectant, preferably, but not limiting to dimethyl sulfoxide from 1% to 10%. Alternatively, dimethyl sulfoxide may also be substituted with human serum albumin. Typically, a cryovial contains from 25 million to 30 million cells per vial. Alternatively, cryovials of up to 5 ml in size may also be used.

The mesenchymal stem cells in cryovials are frozen in a controlled rate freezer until −70 to −90° C. but preferably −90 gradually before transferring into quarantine tank, preferably, but not limiting to a vapour phase liquid nitrogen storage tank.

To prepare a cell-based composition for the treatment of vernal keratoconjunctivitis, the cryopreserved mesenchymal stem cells in cryovials are first thawed at a temperature ranging from 30° C. to 40° C., preferably at 37° C. in a water bath or an incubator for a period from 1 to 5 minutes, more preferably at 2 minutes. Next, the cells are then transferred into new sterile cryovials and are washed with sterile saline, preferably but not limiting to 0.9% sodium chloride. The washed cells in the sterile cryovials will then be centrifuged at a speed ranging from 500×g to 1000×g, preferably at 800×g for a period from 3 to 10 minutes, more preferably for 5 minutes at room temperature, forming a layer of supernatant and a pellet of mesenchymal stem cells.

Typically, the supernatant is removed and discarded, leaving the pellet of mesenchymal stem cells in the cryovial. The pellet of mesenchymal stem cells are then re-suspended with sterile saline at a volume ranging from 5 to 20 ml, preferably at 10 ml, forming a suspension of mesenchymal stem cells.

A cell-based composition is then prepared by infusing the suspension of mesenchymal stem cells into crystalloid to reach a cellular concentration from 0.01 million to 3.0 million cells/ml. The crystalloid includes, but not limiting to normal or half-normal saline or colloid.

Exact amount of cells per kg body weight to be administered into a patient depends on variety of factors including body weight, route of administration, age and gender of the patient, and also the type of mechanism of action targeted. Typically, the therapeutically effective amount of the cell-based composition used for the treatment of vernal keratoconjunctivitis is from to 0.25 million to 3.0 million cells/kg body weight.

The following examples further illustrate but by no means limit the scope of the invention:

Example 1: Collection and Handling of Umbilical Cord Sample

The umbilical cord sample was detached from placenta of a donor post-birth using medical scissors and was immediately submerged in povidone iodine solution for 1-5 minutes to eliminate bacteria and to avoid any risk of contamination. Alternatively, the umbilical may be disinfected using alcohol swab. Upon disinfection, the umbilical cord was then placed in a sterile container of sterile saline solution to maintain moisture. Subsequently, the sterile container was placed into a collection kit and was transported to laboratory using a thermo-insulated bag and kept under a temperature range from 4° C. to 37° C.

The sample was then processed within 48 hours from time of collection.

Example 2: Isolation and Culture of Mesenchymal Stem Cells

First, veins and arteries of the umbilical cord were removed and followed by mincing into 1-2 mm fragments. The fragments were digested with an enzyme, preferably, but not limiting to 0.01% to 0.05% collagenase type II, for a period from 1 to 3 hours, forming a mixture. Next, a centrifugation was carried out to separate the mesenchymal stem cells from the mixture. The mesenchymal stem cells were isolated and then cultured in a growth medium, preferably, but not limiting to Dulbecco's Modified Eagle's Medium (DMEM) which may or may not contain low glucose supplemented with 5-20% animal-free serum and a combination of antibiotics comprising 100 U/mL penicillin, 100 mg/mL streptomycin, 250 ng/mL amphotericin B and 2 mM glutamine. The cultures were maintained at 37° C. in a humidified atmosphere of 5% $CO_2$ and 95% air for 3 days.

Non-adherent cells were discarded and the growth medium was replaced every 3-4 days until the cells reached confluence.

Next, the plastic-adherent mesenchymal stem cells were incubated with trypsin and re-plated at $1\times10^4$ cells/ml for 3-4 passages. The mesenchymal stem cells were then harvested in a culture flasks, thus expanding population of the cells.

FIG. 1 illustrates the morphology of the mesenchymal stem cells.

Example 3: Characterization of Mesenchymal Stem Cells

Immunophenotyping

Figure 2:
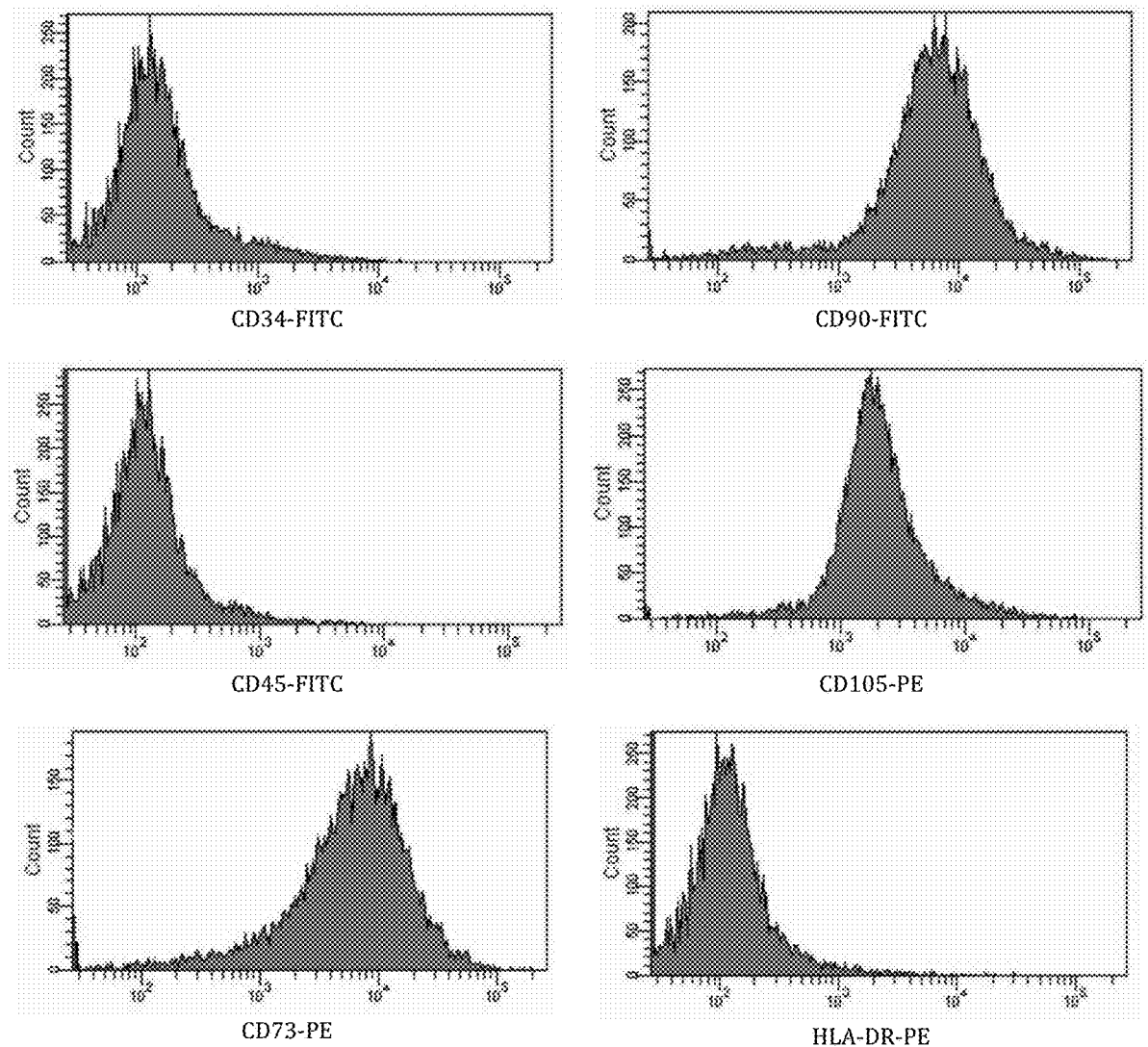
FIG. 2 illustrates immunophenotyping assay results of the mesenchymal stem cells.

The mesenchymal stem cells were immunophenotyped at passage three using isotype (fluorescein isothiocyanate) FITC and (phycoerythrin) PE controls with antigen markers which include CD34, CD45, CD73, CD90, CD105 and HLA-DR. As shown in FIG. 2, the immunophenotyping assay results for the mesenchymal stem cells validate expression for CD73, CD90 and CD105 whilst lacking expression for CD34, CD45 and HLA-DR.

Differentiation Assay

To perform this assay, a selection of specially formulated differentiation medium were used to induce tri-differentiation ability of the mesenchymal stem cells.

Adipogenesis:

The mesenchymal stem cells were treated in adipogenic differentiation medium comprising complete medium supplemented with 1 mM dexamethasone and 0.2 mM indomethacin, 0.01 mg/mL insulin and 0.5 mM 3-isobutil-1-metil-xantina. The medium was replaced every 3 days, and the differentiated cells were subjected to Oil Red O staining after about 14 days of culture.

Chondrogenesis:

The mesenchymal stem cells were cultured in pellet form and maintained in a chemically defined basal medium comprising complete medium supplemented with 50 mg/mL ascorbate-2-phosphate, 1.0 mM sodium piruvate, 40 mg/mL proline, 10 ng/mL transforming growth factor-b3, 6.25 mg/mL human insulin, 6.25 mg/mL transferrin, 6.25 mg/mL bovine insulin, 6.25 mg/mL selenous acid, 1.25 mg/mL linoleic acid, and 5.35 mg/mL bovine serum albumin. Next, the cells were suspended in 1 mL of chondrogenic medium and replaced every 3-4 days. Chondrogenic pellets were harvested after 5 weeks in culture. To assess chondrogenesis, Alcian Blue was used to stain cartilage matrix.

Osteogenesis:

The mesenchymal stem cells were treated in osteogenic differentiation medium comprising complete medium supplemented with 50 mg/mL ascorbate-2-phosphate, 10 mM b-glycerophosphate, and 100 nM dexamethasone. The medium was replaced every 3 days continuously for 2-3 weeks. Alizarin Red S was used to stain matrix mineralization associated with differentiated osteocytes.

Figure 3:
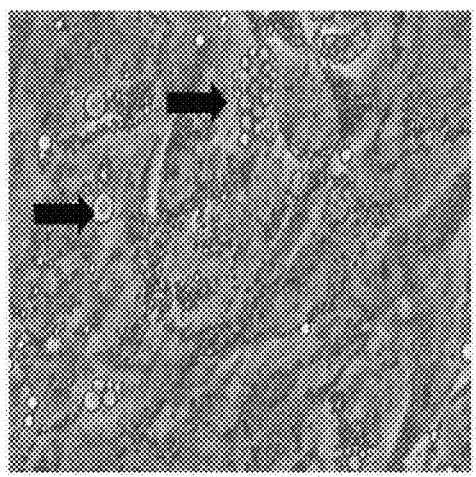
FIG. 3 illustrates adipogenesis, osteogenesis and chondrogenesis of the mesenchymal stem cells respectively.
Figure 3:
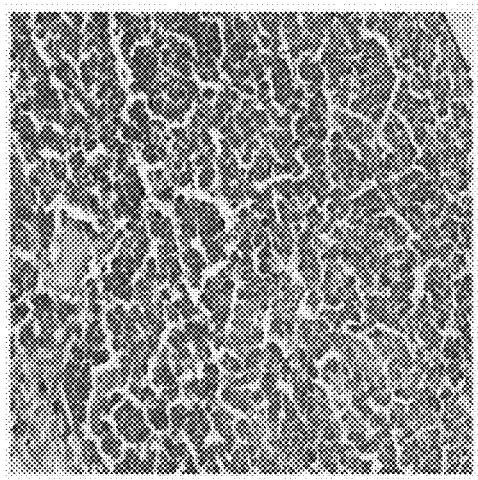
Figure 3:
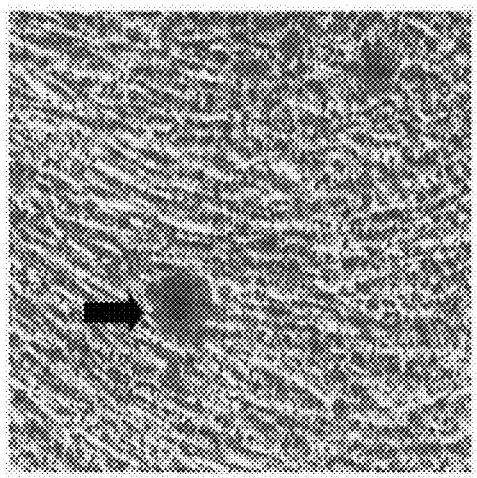

FIG. 3 demonstrates the tri-differentiation ability of the mesenchymal stem cells exhibiting adipogenesis, osteogenesis and chondrogenesis respectively.

Example 4: Cryopreservation of Mesenchymal Stem Cells

Once the population of mesenchymal stem cells was expanded, trypsin was added in to the flasks and incubated at 37° C., for 5 minutes to detach the plastic-adherent mesenchymal stem cells, leaving the cells slightly shrunk. Next, the flasks were gently tapped to dislodge the cells and medium was further added to dilute the trypsin, forming a mesenchymal cell suspension. The cell suspension was then transferred into 50 ml centrifuge tubes and centrifuged at 500 g at a temperature ranging from 18° C. to 30° C. for 10 minutes forming a layer of supernatant with pellet at bottom of the tubes. The supernatant was removed, leaving the pellet of mesenchymal stem cells in the tubes.

The pellet of mesenchymal stem cells were re-suspended in a sterile cryovial containing cryopreservation medium comprising up to 90% animal-free serum and up to 10% dimethyl sulfoxide and were cryopreserved in a controlled freezing gradual rate at −90° C. before being transferred into a quarantine tank at −190° C.

Example 5: Preparation of the Cell-Based Composition for Treatment

The cryopreserved mesenchymal stem cells in cryovials were thawed at 37° C. in a water bath or an incubator for 2 minutes. Next, the cells were then transferred into new sterile cryovials and were washed with 0.9% sodium chloride. The washed cells in the sterile cryovials were then centrifuged at 800×g for 3-10 minutes at room temperature, forming a layer of supernatant and a pellet of mesenchymal stem cells. The supernatant was removed using a sterile syringe, leaving the pellet of mesenchymal stem cells in the cryovial.

The pellet of mesenchymal stem cells was then re-suspended with sterile saline at 10 ml, forming a suspension of mesenchymal stem cells. A cell-based composition was then prepared by infusing the suspension of mesenchymal stem cells into saline at a volume of 250 ml, in a sterile bottle.

Example 6: Treatment Procedure Using the Cell-Based Composition

Treatment using the cell-based composition was carried out on a child male patient 10 years of age afflicted with vernal keratoconjunctivitis. The patient was given a single injection of the cell-based composition at a dose of $75 \times 10^6$ cells.

The treatment procedure began with infusion of 200 ml saline into the patients for a period from 45 to 60 minutes. Next, the cell-based composition which was prepared earlier (as described in Example 5) was infused into the patients for a period from 30 minutes to 2 hours. The bottle containing the cell-based composition was shaken gently every 5 minutes to ensure that the cells are suspended in saline homogenously. When the infusion is almost complete, 50 ml of sterile saline was infused into the bottle containing the cell-based composition to rinse and flush out any remaining cells.

Example 7: Results and Discussion

Figure 4:
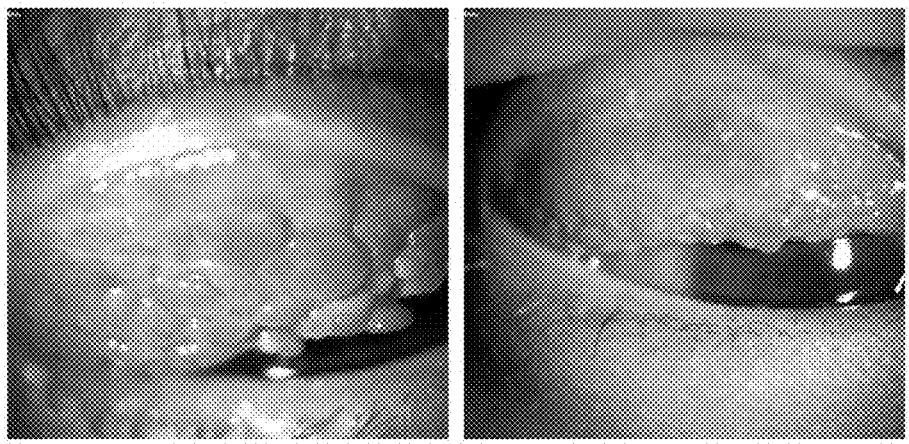
FIG. 4 illustrates symptomatically better and clinically improved condition in right eye of a patient with vernal keratoconjunctivitis after 3 months receiving treatment using cell-based composition.
Figure 5:
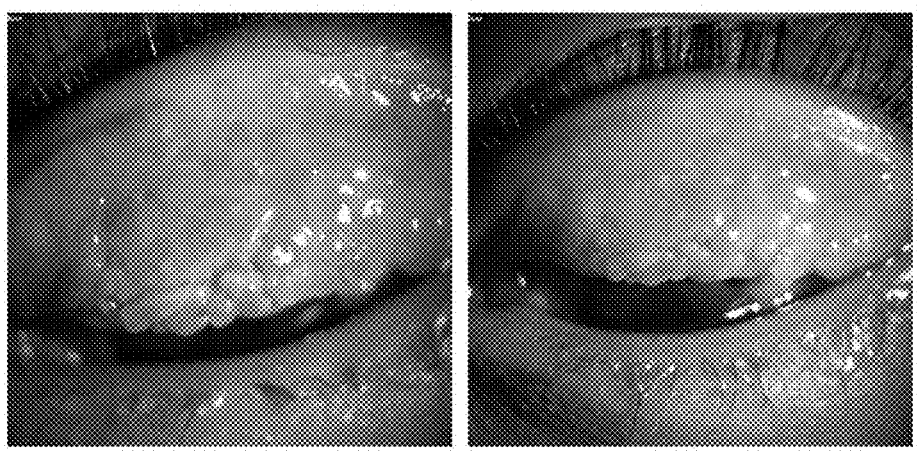
FIG. 5 illustrates symptomatically better and clinically improved condition in left eye of a patient with vernal keratoconjunctivitis after 3 months receiving treatment using cell-based composition.

Following infusion of the cell-based composition, it was found that the vernal keratoconjunctivitis in the patient improved. FIGS. 4-5 demonstrate significant reduction in cobble stones appearance coupled with significant symptomatic relief.

It was noted that the ocular surface of the patient also improved.

Having described preferred embodiments of the present invention with reference to the accompanying drawings, it is not intended that these embodiments and examples illustrate and describe all possible forms of the present invention, and it is to be understood that the present invention is not limited to those precise embodiments, and that various changes and modifications may be effected therein by one skilled in the art without departing from the scope of the invention as defined in the appended claims.

The invention claimed is:

1. A method for the treatment of vernal keratoconjunctivitis in a human subject, said method comprising administering to said subject a therapeutically effective amount of a cell-based composition containing a suspension of mesenchymal stem cells in crystalloid with a cellular concentration from 0.01 million to 3.0 million cells/ml, wherein the cell-based composition is obtained by the steps consisting of digesting a tissue sample that contains mesenchymal stem cells with a digestion enzyme, culturing the mesenchymal stem cells to 70% to 80% confluence, dissociating the cultured mesenchymal stem cells, replating the mesenchymal stem cells, expanding the mesenchymal stem cells, and suspending the expanded mesenchymal stem cells in crystalloid.

2. The method as claimed in claim 1, wherein the cell-based composition is administered by way of intravenous infusion.

3. The method as claimed in claim 2, wherein the infusion is carried out in a period ranging from 30 minutes to 2 hours.

4. The method as claimed in claim 1, wherein the therapeutically effective amount is from 0.25 million to 3.0 million cells/kg body weight.

5. The method as claimed in claim 1, wherein the suspension of mesenchymal stem cells is derived from human umbilical cord, bone marrow, fat tissue, peripheral blood or tooth pulp.

6. The method as claimed in claim 5, wherein the cell-based composition is administered by way of intravenous infusion.

7. The method as claimed in claim 6, wherein the therapeutically effective amount is from 0.25 million to 3.0 million cells/kg body weight.

8. The method as claimed in claim 6, wherein the infusion is carried out in a period ranging from 30 minutes to 2 hours.

9. The method as claimed in claim 1, wherein the suspension of mesenchymal stem cells is positive for a selected group of surface markers including CD73, CD90, and CD105, and negative for a selected group of surface markers including CD34, CD45, and HLA-DR.

10. The method as claimed in claim 9, wherein the cell-based composition is administered by way of intravenous infusion.

11. The method as claimed in claim 10, wherein the therapeutically effective amount is from 0.25 million to 3.0 million cells/kg body weight.

12. The method as claimed in claim 10, wherein the infusion is carried out in a period ranging from 30 minutes to 2 hours.

13. A method for the treatment of vernal keratoconjunctivitis in a human subject, said method comprising administering to said subject a therapeutically effective amount of a cell-based composition containing a suspension of mesenchymal stem cells in crystalloid with a cellular concentration from 0.01 million to 3.0 million cells/ml, wherein the cell-based composition is obtained by the steps consisting of digesting a tissue sample that contains mesenchymal stem cells with a digestion enzyme, culturing the mesenchymal stem cells to 70% to 80% confluence, dissociating the cultured mesenchymal stem cells, replating the mesenchymal stem cells, expanding the mesenchymal stem cells, cryopreserving the expanded mesenchymal stem cells in cryovials each containing from 25 million to 35 million cells, thawing the cryopreserved mesenchymal stem cells, and suspending the thawed mesenchymal stem cells in crystalloid.

14. The method as claimed in claim 13, wherein the cell-based composition is administered by way of intravenous infusion.

15. The method as claimed in claim 14, wherein the therapeutically effective amount is from 0.25 million to 3.0 million cells/kg body weight.

16. The method as claimed in claim 14, wherein the infusion is carried out in a period ranging from 30 minutes to 2 hours.

* * * * *